United States Patent [19]

Feeney

[11] Patent Number: 4,505,707

[45] Date of Patent: Mar. 19, 1985

[54] MALE SANITARY DEVICE

[76] Inventor: Francis T. Feeney, No. 2 Windsor Ct., Lansdale, Pa. 19446

[21] Appl. No.: 421,505

[22] Filed: Sep. 22, 1982

[51] Int. Cl.³ ............................................. A61F 5/44
[52] U.S. Cl. .................................. 604/393; 604/396; 604/401; 604/389; 604/359; 604/387; 604/392; 604/395
[58] Field of Search ................ 604/304, 308, 346–349, 604/351–354, 358, 386, 387, 389, 390, 392–398, 400–402, 385; 128/1 R, 138 R, 132 R

[56] References Cited

U.S. PATENT DOCUMENTS

| 715,112 | 12/1902 | Minard |  |
| 1,989,283 | 1/1935 | Limacher | 604/392 |
| 2,024,491 | 12/1935 | Veysey | 604/308 |
| 3,227,160 | 1/1966 | Younger | 128/171 |
| 3,993,074 | 11/1976 | Murray | 128/286 |
| 4,019,517 | 4/1977 | Glassman | 128/284 |
| 4,022,210 | 5/1977 | Glassman | 604/389 |

FOREIGN PATENT DOCUMENTS 422349 11/1925 Fed. Rep. of Germany ...... 128/286

Primary Examiner—V. Millin
Assistant Examiner—Gregory Beaucage
Attorney, Agent, or Firm—Joseph W. Molasky & Assocs.

[57] ABSTRACT

A male sanitary device which accommodates the anal orifice and lies in the fold between the nates. It is held in the front by an annular member which encircles the external genitalia and it is supported in the back by an appendange or rear member which may be secured to an article of clothing or belt.

10 Claims, 7 Drawing Figures

U.S. Patent   Mar. 19, 1985   Sheet 1 of 2   4,505,707
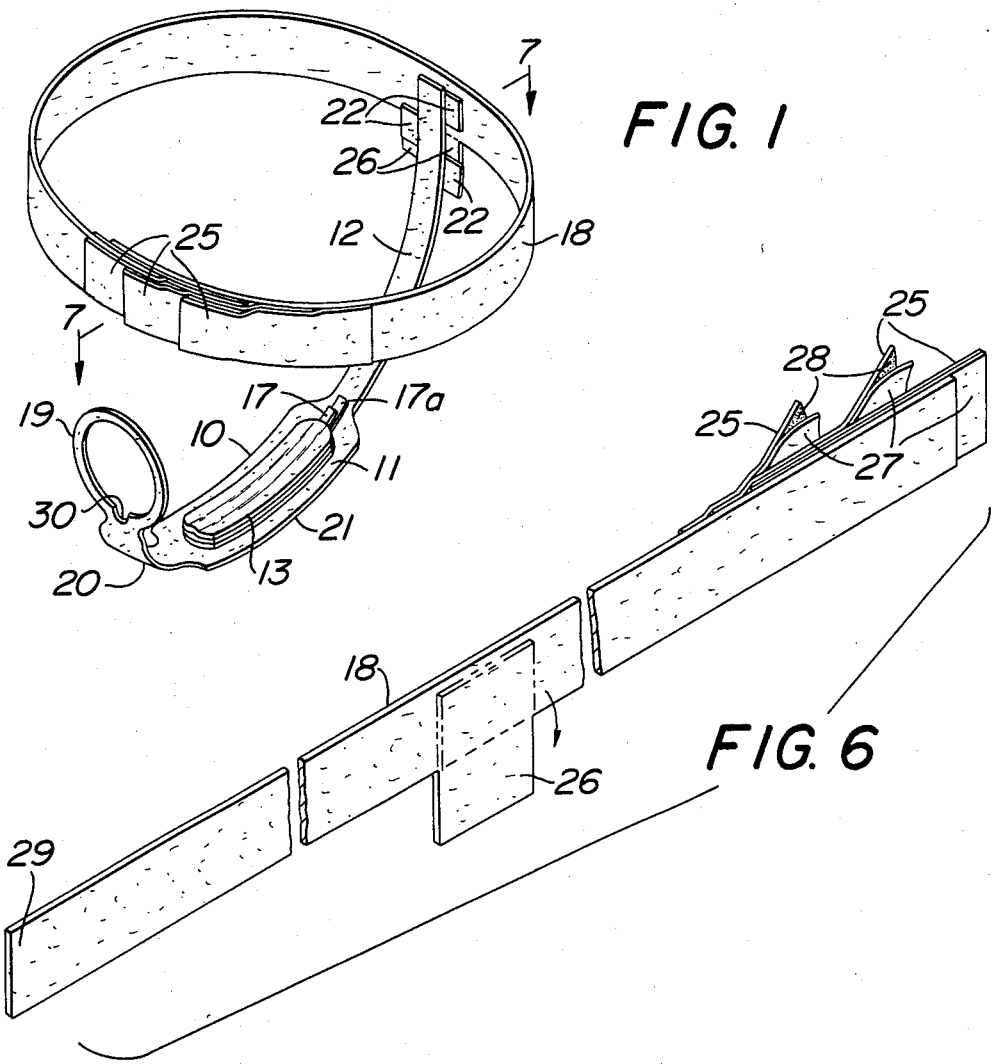
FIG. 1
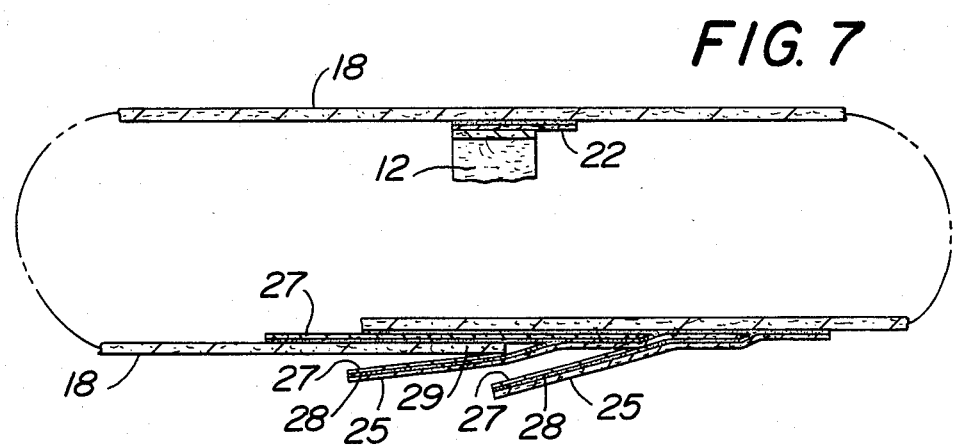
FIG. 6
FIG. 7

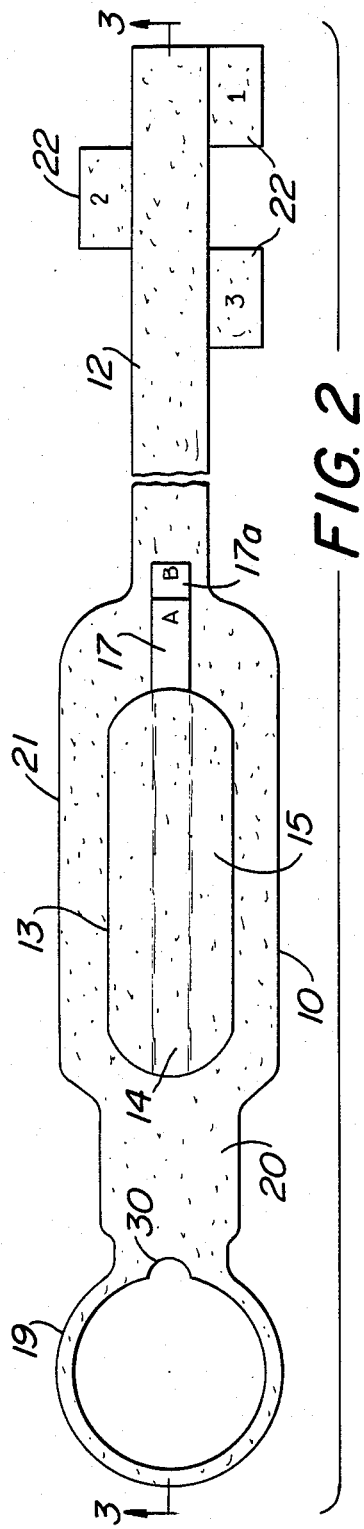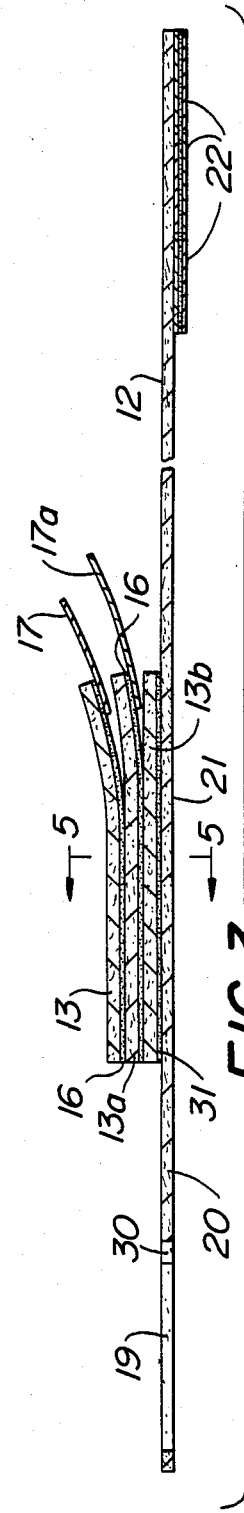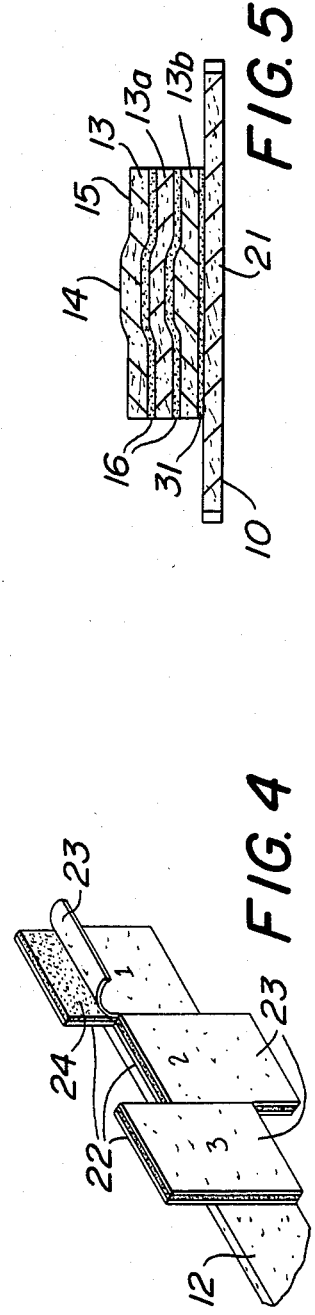

MALE SANITARY DEVICE

This invention relates to a male sanitary device. Specifically, this invention relates to an anal device which relies upon the unique physiognomy of the male form to hold it in place.

More specifically, this invention uses the male genitalia to support the front end of said device, whereas, the back end or rear member may be attached to an article of clothing such as undershorts. Alternatively, in post-operative cases where a hospital gown is worn or clothing cannot be tolerated, a disposable belt may be used to support said rear member. Sanitary pads located between said front end and said rear member are contoured to fit between the buttocks and absorb fluids which escape from the anal orifice as a result of which they are safely and unobstrusively held in place and will not drop, sag, move sideways, backward or forward.

BACKGROUND

Most catamenial devices consist of a pad and fluid impervious support which are held in place by a belt worn around the midsection. However, such devices are an embarrassment to male wearers because they are designed primarily for women and cannot be held in place without a belt. Moreover, the presence of a belt renders them unsuitable for use with abbreviated apparel where a belt or waistband would be visible.

Typical of such a device is the surgical appliance described by M. Younger in U.S. Pat. No. 3,277,160. This consists of a broad band which is secured between the legs of the user by attaching same to the front end and back end of an adjustable belt worn around the waist. When the device is worn by a man said band terminates at the front end just beneath the scrotum to provide a penile opening. Unfortunately, this device does not accommodate itself to the male form and it cannot be held in place via attachment to the male genatalia. Also, said band is uniformly wide from front to back, a feature which renders it uncomfortable to wear. Moreover, it cannot be used without a nondisposable supporting belt and this results in an unseemly appearance when swimming trunks and the like are worn.

THE INVENTION

It is an object of this invention to provide a male sanitary device which can be worn unobstrusively without discomfort.

It is another object of this invention to provide a sanitary device which can be appended to the male genatalia as a means of supporting same.

It is a further object to provide a sanitary device equipped with adhesive means for attaching same to an article of clothing, waistband or disposable belt.

Specifically, the device of this invention is comprised of the following:

(1) an annular front member which encircles the scrotum and penis of the male user;

(2) an elongated central portion for supporting a plurality of contoured absorbent pads superimposed one atop the other; and (3) a rear member equipped with means for detachably securing said rear member to a garment. Said garment may be an article of clothing such as the inside face of undershorts or the like.

When conventional clothing cannot be worn as, for example, when a patient is attired in a hospital gown, said rear member may be attached to a disposable belt or waistband provided for such a purpose. Preferably, said belt is equipped with means for securing same to said rear member as, for example, by providing at about the midpoint on said belt a fold-down tab to provide an additional area for variably adjusting the device to said belt.

The ends of said belt may be secured to one another by a variety of means as, for example, by a buckle assembly, snaps or Velcro fasteners; however, a preferred holding means, particularly where the belt is of the disposable variety, are conventional adhesive fasteners. Such fasteners provide a temporary bond of more-than-adequate strength while, at the same time, they may be easily separated for refitting and re-use without any discernible loss in holding power.

THE DRAWINGS

FIG. 1 is an isometric view of the sanitary device of this invention equipped with a belt.

FIG. 2 is a plan view of the inside face of the sanitary device of this invention.

FIG. 3 is a sectional view of the device shown in FIG. 2 taken on line 3—3.

FIG. 4 is a fragmentary isometric view of a portion of the device shown in FIG. 2 illustrating the outside face of a rear member.

FIG. 5 is a sectional view of the device shown in FIG. 3 taken on line 5—5.

FIG. 6 is an isometric view illustrating the belt shown in FIG. 1 in an open mode.

FIG. 7 is a fragmentary top view of FIG. 1 taken on line 7—7 illustrating said belt in a closed mode.

DESCRIPTION OF THE INVENTION

The present device 10 (FIGS. 1 & 3) is formed from sheet material which may be fluid impervious. It consists essentially of an annular front member 19, an elongated central portion 21 and a rear member 12 equipped with adhesive tabs 22 which are used to secure said rear member to a garment or belt. The front member 19 encircles the genitalia of the male user and the elongated central portion 21 provides support for fluid absorbent pads which contact the anus. A connecting member 20 fits the user's crotch and joins said front member to said central portion.

In FIG. 1 the sanitary device 10 is shown with a disposable belt 18 which is worn around the user's waist or mid-section. On its inside face 11 there are arranged in layers several fluid absorbent pads 13 which lie flat and are essentially rectangular in appearance (FIG. 2); however, a preferred embodiment provides for pads which are slightly elevated or thickest along their longitudinal centers so as to better fit the buttocks and provide increased absorbency where it is most needed. This is illustrated by FIG. 5 which shows a plurality of like-sized pads superimposed one atop the other with their centers 14 raised slightly above the surrounding surface 15. Disposed between each pad is a fluid impervious barrier strip 16 having insert tabs 17 and 17a appended thereto for the removal of one pad from another (FIG. 3). Each barrier strip is securely bonded to an overlying pad but only lightly secured to an underlying pad by spot adhesives or heat compression or the like. As a result, one pad can be separated from another by pulling upwards on said tab and rupturing the light seal which joins said barrier strip to the underlying pad. The bottom-most pad 13b in this arrangement (FIG. 3) is not removable but is disposable and, therefore, it may be securely bonded to the inside face 11 of the device as, for example, by the use of a strong adhesive 31. Alternatively, the bottom-most pad 13b and the device may be fabricated from the same sheet material as a result of which they are integrally joined. If desired, the pads may be impregnated with deodorant or medication to alleviate conditions associated with rectal surgery or hemmorrhoids or the like.

The pads must be capable of absorbing both an occasional discharge and a flow of rectal fluids; therefore, it is desirable that they be derived from fluid pervious materials such as cotton or cellulose and the like. The dimensions are not critical but it is preferred that they measure from about 0.125–0.75 inches in thickness. Moreover, when increased absorbency is required it is desirable that they measure from about 0.125–0.25 inches along their periphery to about 0.25–0.75 inches along their longitudinal centers.

FIG. 6 illustrates the belt 18 which is used to support the present device when it is not secured to an article of clothing. Said belt is an elongated strap of indeterminate length. Preferably, it is narrow and measures about 1–2 inches in width. On its inside face, at about the midpoint, there is provided a fold-down tab 26 for adjustably securing same to the rear member 12 of said device. A fragmentary view of said rear member is shown in FIG. 4. The device 10 is made longer or shorter by peeling away the cover 23 from tab 1, tab 2 or tab 3 of rear member 12 (FIG. 4) and impressing the adhesive which is thus exposed to fold-down tab 26.

The belt also contains overlapping tabs 25 (FIG. 6) at one end to provide variable means for adjusting said belt to the wearer's waist. Said belt is lengthened or shortened by separating the protective cover 27 from the underlying adhesive 28 and adjoining the latter to belt end 29 by the application of slight pressure. FIG. 6 shows said belt in an open mode, that is, prior to joining belt end 29 with tab 25. FIG. 7 illustrates said belt in a closed mode with end 29 adhesively engaged to tab 25 as it is intended to be worn.

The device 10 is applied by holding it pad-side-up and placing the annular front member 19 around both penis and scrotum while fitting the raphe into the semi-circular recess which appears as dimple 30 in FIGS. 1 and 2. The scrotum is divided into lateral portions by a seam which extends from the underside of the penis to the anus. This seam is defined in medical parlance as a raphe and dimple 30 accommodates this anatomical feature.

After the front end has been secured the device 10 is brought down between the legs and pushed rearward so as to bring central portion 21 and pad 13 into contact with the anus. The pad 13 is then fitted into the fold between the buttocks, adjustments are made for a snug fit, and the device 10 is secured at its back end by impressing adhesive segment 24 onto an undergarment or article of clothing.

When pad 13 becomes soiled it is removed by pulling upward on tab 17 to expose new pad 13a and the device is refitted in the manner hereinbefore described. When pad 13a becomes soiled it is removed by pulling upward on tab 17a to expose pad 13b.

When no undergarment or clothing is worn the correct fit is approximated and the device 10 is first secured at its back end by impressing the adhesive portion of rear member 12, that is, adhesive 24 of rear tab 22, onto folddown tab 26 of belt 18. Said belt is then secured around the waist by joining belt end 29 to adhesive portion 28 (FIG. 6). The annular ring 19 is drawn frontwards through the legs and the absorbent pad on central portion 21 is impressed into the anal orifice. After said pad has been comfortably fitted the device is secured at its front end by placing the annular member 19 around the genatalia.

This invention has been described by embodiments and illustrations which depict three absorbent pads in a stacked arrangement; however, it will be understood by those skilled in the art that a single pad or any plurality of pads can be utilized without departing from this invention. Moreover, any modifications of this invention which are within the skill of the artisan to effect should be considered an obvious extension of the concept herein described and should fall within the scope of the appended claims.

What is claimed is:

1. A contoured sanitary device for a man comprising:
    (1) an annular front member constituting the sole support for said device by encircling the scrotum and penis;
    (2) an elongated central portion for supporting a plurality of contoured absorbent pads superimposed one atop the other; and
    (3) a rear member equipped with means for detachably securing same to a garment and said rear member providing the sole support means for said device.

2. The device of claim 1 wherein the means for securing said rear member consists of an adhesive area covered by one or more protective tabs which may be removed to expose portions of said adhesive.

3. The device of claim 1 wherein said garment is a pair of undershorts.

4. The device of claim 1 wherein each of said pads is attached to a tab which may be used to separate one superimposed pad from an underlying pad.

5. The device of claim 1 wherein said pads are contoured to fit the anal orifice and are of lesser dimension than the elongated central portion to which they are adjoined.

6. The device of laim 1 wherein said annular front member includes a semi-circular recess to accommodate the raphe of the male user.

7. The device of claim 1 wherein said pads are impregnated with a medicinal agent or deodorant.

8. The device of claim 1 wherein said garment is a belt which encircles the waist, said belt having a folddown tab on its inside face located at about its midpoint for detachably securing same to said rear member.

9. The device of claim 8 wherein said belt has a front portion equipped with means for adjustably securing the ends of said belt to one another.

10. The device of claim 9 wherein the means for securing the ends of said belt to one another is an adhesive area covered by a protective tab which may be removed to expose said adhesive.

* * * * *